United States Patent
Lu

(10) Patent No.: US 9,572,783 B1
(45) Date of Patent: Feb. 21, 2017

(54) USE OF XANTHOPHYLLS FOR THE TREATMENT OF CANCERS

(71) Applicant: Chuen Wei Lu, Taoyuan (TW)

(72) Inventor: Chuen Wei Lu, Taoyuan (TW)

( * ) Notice: Subject to any disclaimer, the term of this patent is extended or adjusted under 35 U.S.C. 154(b) by 0 days.

(21) Appl. No.: 14/878,653

(22) Filed: Oct. 8, 2015

(51) Int. Cl.
| | | |
|---|---|---|
| A61K 31/12 | (2006.01) | |
| A61K 31/122 | (2006.01) | |
| A61K 45/06 | (2006.01) | |

(52) U.S. Cl.
CPC ............ *A61K 31/122* (2013.01); *A61K 45/06* (2013.01)

(58) Field of Classification Search
USPC ........................................................ 514/691
See application file for complete search history.

(56) References Cited

U.S. PATENT DOCUMENTS

| | | | |
|---|---|---|---|
| 6,277,417 B1 | 8/2001 | Anderson | |
| 6,773,708 B1 | 8/2004 | Lignell et al. | |
| 6,784,351 B2* | 8/2004 | Hauptmann | C12N 15/8243 426/531 |
| 8,058,243 B2 | 11/2011 | Tyers et al. | |
| 8,632,825 B2 | 1/2014 | Velasco Diez et al. | |
| 2007/0259843 A1 | 11/2007 | Marcus et al. | |
| 2013/0172407 A1* | 7/2013 | Kuo | A61K 31/01 514/475 |
| 2013/0302319 A1 | 11/2013 | Rosen et al. | |

FOREIGN PATENT DOCUMENTS

| | | |
|---|---|---|
| CN | 1 01 361 726 A | 2/2009 |
| EP | 1 867 327 A1 | 12/2007 |
| WO | 02/05827 A2 | 1/2002 |
| WO | 03/041695 A1 | 5/2003 |
| WO | 2006/099015 A2 | 9/2006 |

OTHER PUBLICATIONS

Yasui et al., Chem. Biol. Interact., 2011, 193(1):79-87.*
Palozza et al., Cancer Lett, 2009, 283(21): 108-17.*
Jyonouchi et al., Nutr. Cancer, 2000, 36(1): 59-65.*
Rao et al., Journal of Agricultural and Food Chemistry, 2013, 61(16): 3842-3851.*
Xiang et al. CAS: 161: 227115, 2014.*
Okada's CAS: 144: 81239, 2006.*
Tanaka et al, Molecules, 2012, 17:3202-3242.*
Kenneth Aldape et al., "Glioblastoma: pathology, molecular mechanisms and markers", Acta neuropathologica, May 6, 2015.
Constantinos Alifieris et al., "Glioblastoma multiforme: Pathogenesis and treatment", Pharmacology & therapeutics, 2015.
Tobias Else et al., "Adrenocortical carcinoma", Endocrine reviews, 2014, pp. 282-326, vol. 35, No. 2.
Lori A. Erickson et al., "Adrenocortical carcinoma: review and update", Advances in anatomic pathology, May 2014, pp. 151-159, vol. 21, No. 3.

Higuera-Ciapara, I. et al., "Astaxanthin: a review of its chemistry and applications", Critical reviews in food science and nutrition, 2006, pp. 185-196, vol. 46.
Ghazi Hussein, et al., "Astaxanthin, a carotenoid with potential in human health and nutrition", Journal of natural products, 2006, pp. 443-449, vol. 69.
K. Kavitha, et al., "Astaxanthin inhibits NF-κB and Wnt/β-catenin signaling pathways via inactivation of Erk/MAPK and PI3K/Akt to induce intrinsic apoptosis in a hamster model of oral cancer", Biochimica et biophysica acta, 2013, pp. 4433-4444, vol. 1830.
Khan, Sanjoy K. et al., "Novel astaxanthin prodrug (CDX-085) attenuates thrombosis in a mouse model", Thrombosis research, 2010, pp. 299-305, vol. 126.
Kim, You Jung et al., "Protection against oxidative stress, inflammation, and apoptosis of high-glucose-exposed proximal tubular epithelial cells by astaxanthin", Journal of agricultural and food chemistry, 2009. pp. 8793-8797, vol. 57.
Kowshik, J. et al., "Astaxanthin inhibits JAK/STAT-3 signaling to abrogate cell proliferation, invasion and angiogenesis in a hamster model of oral cancer", PLOS one, Oct. 2014, vol. 9, No. 10, e109114.
Park, Jean Soon et al., "Astaxanthin decreased oxidative stress and inflammation and enhanced immune response in humans", Nutrition & metabolism, 2010, vol. 7, No. 18.
Sasaki, Yasuto et al., "Astaxanthin inhibits thrombosis in cerebral vessels of stroke-prone spontaneously hypertensive rats", Nutrition research, 2011, pp. 784-789, vol. 31.
Song, Xiao-Dong et al., "Astaxanthin induces mitochondria-mediated apoptosis in rat hepatocellular carcinoma CBRH-7919 cells", Biological & pharmaceutical bulletin, Jun. 2011, pp. 839-844, vol. 34, No. 6.
Stupp, Roger et al., "Effects of radiotherapy with concomitant and adjuvant temozolomide versus radiotherapy alone on survival in glioblastoma in a randomised phase III study: 5-year analysis of the EORTC-NCIC trial", Lancet Oncology, 2009, pp. 459-466, vol. 10.
Wu, Qi et al., "Astaxanthin activates nuclear factor erythroid-related factor 2 and the antioxidant responsive element (Nrf2-ARE) pathway in the brain after subarachnoid hemorrhage in rats and attenuates early brain injury", Marine drugs, 2014, pp. 6125-6141, vol. 12.
Zhang, Xiang-Sheng et al., "Astaxanthin offers neuroprotection and reduces neuroinflammation in experimental subarachnoid hemorrhage", Journal of surgical research, 2014, pp. 206-213, vol. 192.
Zhang, Xiang-Sheng et al., "Amelioration of oxidative stress and protection against early brain injury by astaxanthin after experimental subarachnoid hemorrhage", Journal of neurosurgery, 2014, pp. 42-54, vol. 121.
Communication, dated Feb. 9, 2016, issued by the European Patent Office in counterpart European Patent Application No. 15188975.5.

* cited by examiner

*Primary Examiner* — Rei-Tsang Shiao
(74) *Attorney, Agent, or Firm* — Sughrue Mion, PLLC

(57) ABSTRACT

The present invention relates to a novel use of xanthophylls, particularly astaxanthin and/or an ester thereof, for inhibiting tumor cell growth. Therefore, the present invention provides a method for preventing or treating cancers, comprising administering to a subject in need thereof a composition comprising a therapeutically effective amount of at least one type of xanthophyll.

15 Claims, 8 Drawing Sheets
(2 of 8 Drawing Sheet(s) Filed in Color)

** P<0.01
*** P<0.001 comparing with control (DMSO) group

\*\*P<0.01 comparing with control (DMSO) group

USE OF XANTHOPHYLLS FOR THE TREATMENT OF CANCERS

FIELD OF THE INVENTION

The present invention relates to a novel use of xanthophylls for treating cancers, particularly, adrenocortical carcinoma, osteosarcoma or glioblastoma multiforme.

BACKGROUND OF THE INVENTION

Xanthophylls are a large group of carotenoids containing oxygen in molecules in addition to carbon and hydrogen. Astaxanthin, a xanthophyll carotenoid, is a natural antioxidant that is produced in many biological organisms (Hussein et al., 2006). It occurs naturally in certain algae and causes the pink or red color in salmon, trout, lobster, shrimp, and other seafood. While astaxanthin is a natural dietary component, it can also be used as a food supplement. The U.S. Food and Drug Administration (FDA) has approved astaxanthin as a food coloring (or color additive) for specific uses in animal and fish foods. The European Commission considers it a food dye and it is given the E number E161j. Natural astaxanthin is generally recognized as safe (GRAS) by the FDA, but as a food coloring in the United States it is restricted to use in animal food only.

The biological activities of astaxanthin have been tested in many animal models and clinical tests. Astaxanthin blocks the aerobic metabolism-generated free radicals, such as hydroxyls, peroxides and reactive oxygen species, thus preventing abnormal DNA damage (Higuera-Ciapara et al., 2006). Further studies have also demonstrated that astaxanthin contributes to immune response (Kim et al., 2009; Park et al., 2010). Participants who received astaxanthin daily for 8 weeks showed upregulating mitogen-induced lymphoproliferation, increased natural killer cell cytotoxic activity, and increased total T and B leukocytes. U.S. Pat. No. 6,773,708 B1 discloses the use of xanthophylls such as astaxanthin for the treatment of autoimmune diseases, chronic viral and intracellular bacterial infections by suppressing excessive Th1 cell mediated immune responses, and stimulating Th2 cell mediated immune responses in a patient during ongoing infection and/or inflammation in said patient.

Oral administration of astaxanthin inhibits thrombosis in vascular endothelial injury mouse models and in stroke-prone spontaneously hypertensive rats (Khan et al., 2010; Sasaki et al., 2011). CN 101361726 A discloses that astaxanthin can improve behavioral symptoms caused by cerebral ischemia reperfusion injury of rats, decrease the volume of cerebral infarction and lower the cerebral edema of cerebral ischemic rats, and thus can be used for preparing drugs for preventing and curing brain stroke.

In addition, astaxanthin also protects neuronal cells. Treatment with astaxanthin ameliorates neuroinflammation and early brain injury by activating nuclear factor erythroid-related factor 2 and the antioxidant responsive element (Nrf2-ARE) pathway after subarachnoid hemorrhage (Wu et al., 2014; Zhang et al., 2014a; Zhang et al., 2014b). More importantly, astaxanthin penetrates the natural blood-brain barrier (BBB) and thus can be used in treating brain neuronal diseases (Wu et al., 2014). EP1 867 327 A1 discloses a neurocyte protective agent comprising astaxanthin and/or an ester thereof capable of alleviating mitochondrial dysfunction and oxidative stress in neurocytes. The neurocyte protective agent is effective in protecting against the degeneration of dopaminergic neurons of the substantia nigra and noradrenergic neurons of the locus ceruleus, and it is suggested that the neurocyte protective agent can be used for Parkinson's disease.

Astaxanthin is also suggested as a potential anti-tumor compound. It inhibits hamster oral cancer cell growth by blocking STAT, ERK or PI3K/Akt signaling (Kavitha et al., 2013; Kowshik et al., 2014). It was also reported that the treatment of astaxanthin induces mitochondria-depended apoptosis in hepatocellular carcinoma cells (Song et al., 2011). U.S. Pat. No. 6,277,417 B1 discloses that astaxanthin can inhibit the activity of the enzyme 5α-reductase and thus suggests that it can be used for treating or preventing disorders resulting from the activity of the enzyme, in particular benign prostate hyperplasia and prostate cancer.

The adrenal gland, located superiorly to the kidney, consists of the outer adrenal cortex and the inner medulla parts (Else et al., 2014). The adrenal cortex secretes several steroids such as glucocorticoid and mineralocorticoid to regulate the metabolic homeostasis in the body. Adrenocortical carcinoma is a rare disease, with incidence of 1 to 2 per million people every year. It is an aggressive tumor and is often metastasized to other organs, and the overall survival rate is only 20-35% within 5 years. Tumors occurring in the adrenal cortex may induce aberrant secretion of steroids and show symptoms similar to Cushing's syndrome and virilization (Erickson et al., 2014). Several methods are used in the treatment of adrenocortical carcinoma, e.g., complete surgical excision, radiation therapy and combined chemotherapy (the combination of anti-tumor drugs: cisplatin, doxorubicin and etoposide). To date, there is no single method that can effectively block adrenocortical tumor cell growth. It is desirable to develop a therapeutic agent that can safely and effectively treat adrenocortical carcinoma.

Osteosarcoma is the most common histological form of primary bone cancer. It is most prevalent in children and young adults. Mifamurtide (MEPACT®) is currently approved in Europe for the treatment of osteosarcoma. A combination of high-dose methotrexate with leucovorin rescue, intra-arterial cisplatin, adriamycin, ifosfamide with mesna, BCD (bleomycin, cyclophosphamide, dactinomycin), etoposide, and muramyl tripeptide may also be used for the treatment of osteosarcoma.

Glioblastoma multiforme (GBM) is one of the most severe malignant gliomas. GBM is considered incurable, and is associated with high morbidity and mortality, with a median survival of 15 months following several treatments (Aldape et al., 2015; Alifieris and Trafalis, 2015). Temozolomide (TEMODAR®) is currently approved in Europe and the United States for the treatment of GBM. Temozolomide is an alkylating drug indicated for the treatment of adult patients with newly diagnosed GBM concomitantly with radiation therapy and then as maintenance treatment. Several aggressive combination therapies are currently used in treating GBM, such as maximal-safe surgical resection, radiation therapy and temozolomide treatment (Stupp et al., 2009). Many GBM patients respond poorly to the conventional chemotherapy and radiation therapy. The prognosis falls in a poor survival range of 12-15 months (median 14.6 months).

U.S. Pat. No. 8,632,825 B2 discloses the use of tetrahydrocannabinol (THC) and cannabidiol (CBD) in the manufacture of a medicament for use in the treatment of GBM. U.S. Pat. No. 8,058,243 B2 discloses a method for treating a glioblastoma cancer involving neural precursor cells, early neural progenitor cells, neural stem cells (NSCs) or a combination thereof, the method comprising administering to a subject in need thereof a therapeutically effective amount of a composition comprising ifenprodil. Up to now, there is no single compound that can efficiently inhibit GBM tumor growth without other anti-tumor drugs.

SUMMARY OF THE INVENTION

It is an objective of the present invention to provide methods and/or medicaments for preventing or treating cancer selected from the group consisting of adrenal cancer, bone cancer and brain cancer.

One aspect of the invention is to provide a method for inhibiting tumor cell growth, comprising contacting the tumor cell with a composition comprising a therapeutically effective amount of at least one type of xanthophyll.

In a preferred embodiment of the invention, the tumor cell is an adrenal tumor cell.

In a preferred embodiment of the invention, the tumor cell is a bone tumor cell.

In a preferred embodiment of the invention, the tumor cell is a brain tumor cell.

Another aspect of the invention is to provide a method for preventing or treating cancer selected from the group consisting of adrenal cancer, bone cancer and brain cancer, comprising administering to a subject in need thereof a composition comprising a therapeutically effective amount of at least one type of xanthophyll.

The present invention also provides a composition for preventing or treating cancer selected from the group consisting of adrenal cancer, bone cancer and brain cancer, comprising a therapeutically effective amount of at least one type of xanthophyll and a physiologically acceptable carrier.

The present invention further provides a use of xanthophylls in the manufacture of a medicament for preventing or treating cancer selected from the group consisting of adrenal cancer, bone cancer and brain cancer.

In a preferred embodiment of the invention, the adrenal cancer is selected from the group consisting of adrenocortical adenoma, adrenocortical carcinoma, neuroblastoma and pheochromocytoma.

In a more preferred embodiment of the invention, the adrenal cancer is adrenocortical carcinoma.

In a preferred embodiment of the invention, the bone cancer is selected from the group consisting of osteoma, osteoid osteoma, osteochondroma, osteoblastoma, enchondroma, giant cell tumor of bone, aneurysmal bone cyst, fibrous dysplasia of bone, osteosarcoma, chondrosarcoma, Ewing's sarcoma and fibrosarcoma.

In a more preferred embodiment of the invention, the bone cancer is osteosarcoma.

In a preferred embodiment of the invention, the brain cancer is selected from the group consisting of gliomas, meningiomas, pituitary adenomas and nerve sheath tumors, preferably anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme (GBM), gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma.

In a more preferred embodiment of the invention, the brain cancer is glioblastoma multiforme.

In a preferred embodiment of the invention, the xanthophyll is astazanthin and/or an ester thereof.

In a preferred embodiment of the invention, the xanthophylls are derived from a natural source, such as a culture of the algae *Haematococcus* sp.

In a more preferred embodiment of the invention, the algae *Haematococcus* sp. is *Haemotococcus pluvialis*.

In another preferred embodiment of the invention, the xanthophylls are chemically synthesized.

In a preferred embodiment of the invention, the therapeutically effective amount of xanthophylls is from about 0.1 mg to about 10 g per day in case of oral administration, or about 0.01 mg to about 5 g per day in case of parenteral administration.

The composition or medicament of the invention can be used alone or in combination with other treatments. In one preferred embodiment, the composition or medicament is for use without radiation therapy and/or chemotherapy. In another preferred embodiment, the composition or medicament is for use in combination with radiation therapy and/or chemotherapy. In a further preferred embodiment, the composition or medicament is administered simultaneously or separately with one or more therapeutic agents for preventing or treating cancer selected from the group consisting of adrenal cancer, bone cancer and brain cancer or managing the symptoms or complications of adrenal cancer, bone cancer and brain cancer.

In a preferred embodiment of the invention, the cancer has been surgically removed from the subject.

The present invention is described in detail in the following sections. Other characterizations, purposes and advantages of the present invention can be easily found in the detailed descriptions and claims of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
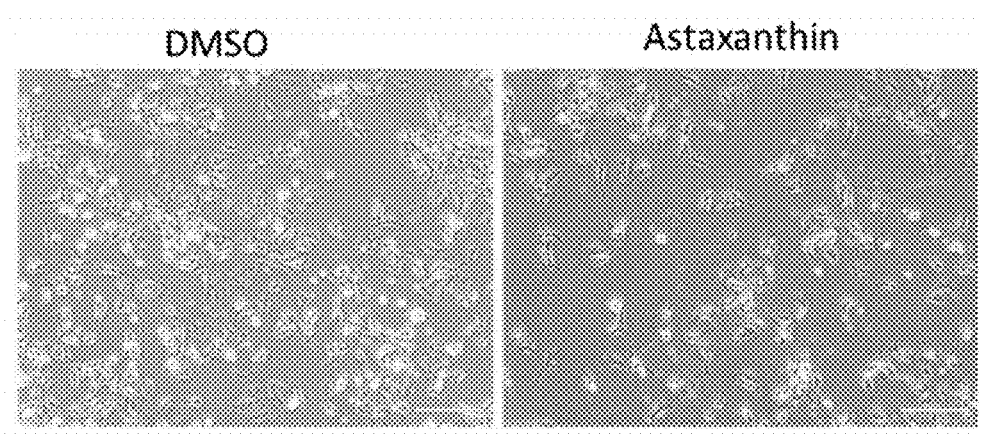
FIGS. 1A and 1B show the bright field microscopy of Y1 cells treated with DMSO (control) or 40 µM astaxanthin, for 24 (A) or 48 (B) hours.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The term "adrenocortical carcinoma (ACC)" as used herein refers to an aggressive cancer originating in the cortex (steroid hormone-producing tissue) of the adrenal gland. Adrenocortical carcinoma may present differently in children and adults. Most tumors in children are functional, and virilization is by far the most common presenting symptom, followed by Cushing's syndrome and precocious puberty. Among adults presenting hormonal syndromes, Cushing's syndrome alone is most common, followed by mixed Cushing's and virilization (glucocorticoid and androgen overproduction). Feminization and Conn syndrome (mineralocorticoid excess) occur in less than 10% of cases. Rarely, pheochromocytoma-like hypersecretion of catecholamines has been reported in adrenocortical cancers. Non-functional tumors (about 40%, authorities vary) usually present with abdominal or flank pain, varicocele and renal vein thrombosis or they may be asymptomatic and detected incidentally.

The term "adrenal cancer" includes, but is not limited to adrenocortical adenoma, adrenocortical carcinoma, neuroblastoma and pheochromocytoma.

The term "bone cancer" includes, but is not limited to osteoma, osteoid osteoma, osteochondroma, osteoblastoma, enchondroma, giant cell tumor of bone, aneurysmal bone cyst, fibrous dysplasia of bone, osteosarcoma, chondrosarcoma, Ewing's sarcoma and fibrosarcoma.

The term "osteosarcoma" refers to a cancerous tumor in a bone. Specifically, it is an aggressive malignant neoplasm that arises from primitive transformed cells of mesenchymal origin (and thus a sarcoma) and that exhibits osteoblastic differentiation and produces malignant osteoid.

The term "brain cancer" includes, but is not limited to, gliomas, meningiomas, pituitary adenomas and nerve sheath tumors, preferably anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme (GBM), gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma.

The term "glioblastoma multiforme (GBM)" refers to the highest grade glioma (grade IV) tumor found in humans. GBM also refers to "glioblastoma" under WHO classification. Glioblastomas arise from normal brain tissue. They may invade and migrate away from the main tumor within the brain; however, glioblastoma will rarely spread elsewhere in the body. There are two subtypes of glioblastoma: de novo (new or primary) and secondary. De novo tumors arise quickly and tend to make their presence known abruptly. They are the most common, and a very aggressive form of glioblastoma. De novo tumors account for the majority of glioblastomas in persons aged 55 and older. Secondary glioblastomas, most often found in patients aged 45 and younger, typically start as low-grade or mid-grade astrocytoma which have been genetically programmed to eventually transform into malignant, rapidly growing glioblastomas.

The term "radiation therapy" refers to a type of cancer treatment that uses high-energy radiation to kill cancer cells or shrink tumors. The radiation dose used in radiation therapy is measured in gray (Gy), and varies depending on the type and stage of cancer being treated.

The term "chemotherapy" includes, but is not limited to, the administration of a chemotherapeutic compound such as adriamycin, cisplatin, doxorubicin, etoposide, fluoropyrimidine, irinotecan, oxaliplatin, taxol, topotecan, etc.

The term "xanthophylls" as used herein refers to a large group of carotenoids containing oxygen in molecules, in addition to carbon and hydrogen or derivatives thereof. The carotenoids are produced de novo by plants, fungi and some bacteria. In a preferred embodiment of the invention, the xanthophyll is astaxanthin or an ester thereof.

Astaxanthin and/or an ester thereof contained in the composition or medicament of the present invention is a carotenoid represented by the following formula:

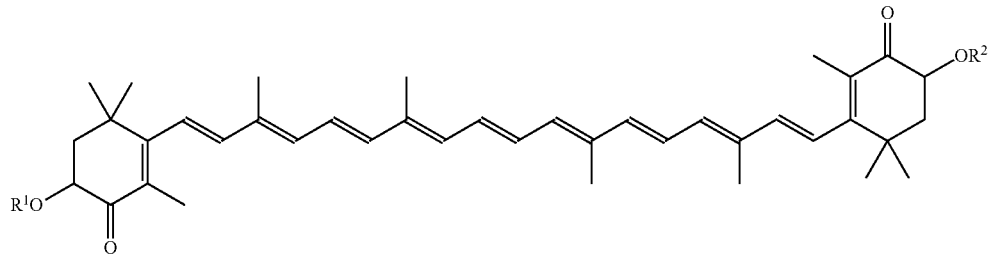

wherein $R^1$ and $R^2$ are both hydrogen in the case of astaxanthin, and $R^1$ and $R^2$ are each independently a hydrogen atom or a fatty acid residue provided that at least one of $R^1$ and $R^2$ is a fatty acid residue in the case of an ester of astaxanthin. Examples of the fatty acid residue in the ester of astaxanthin include, but are not limited to, saturated fatty acids such as palmitic acid and stearic acid or unsaturated fatty acids such as oleic acid, linoleic acid, α-linolenic acid, γ-linolenic acid, bishomo-γ-linolenic acid, arachidonic acid, eicosapentaenoic acid, and docosahexaenoic acid. The astaxanthin ester used in the present invention can be any mono- or di-ester, homogeneous or nonhomogeneous. Astaxanthin has a structure in which an additional oxo group and an additional hydroxy group are present at each end of a β-carotene molecule, so that unlike for β-carotene, the stability of the molecule is low. On the other hand, an ester form (e.g., as obtained in an extract from hill) in which the hydroxy groups at both ends are esterified with an unsaturated fatty acid is more stable.

Astaxanthin and/or an ester thereof used in the present invention may be chemically synthesized or derived from a naturally-occurring product. Examples of the naturally-occurring products in the latter case include red yeast; the shell of crustaceans such as Tigriopus (red water flea) and hills; and microalgae such as green algae, which contain astaxanthin and/or an ester thereof. In the present invention, as long as the properties of astaxanthin and/or esters thereof can be utilized, any extract containing astaxanthin and/or esters thereof produced by any method can be used. Generally, extracts from those naturally-occurring products can be used, and the extracts may be crude or purified if necessary. In the present invention, a crude extract or a crushed powder of naturally-occurring products, or a purified product or a chemically synthesized product, if necessary, that contains such astaxanthin and/or esters thereof can be used either alone or in combination. In view of the chemical stability, an ester form of astaxanthin is preferably used.

The term "preventing" or "prophylaxis" as used herein refers to delaying the onset of symptoms of a susceptible subject, reducing the occurrence of a disorder or condition, or inhibiting the occurrence of the disorder or condition, or arresting the development of the disorder or condition.

The term "treating" or "treatment" as used herein denotes alleviating, relieving, reversing and/or improving a disorder or condition or one or more symptoms thereof, or stopping the symptoms of the disease or condition in a susceptible subject.

The term "subject" as used herein denotes animals, especially mammals. In one preferred embodiment, the term "subject" denotes "humans."

The term "therapeutically effective amount" as used herein refers to the amount of an active ingredient used alone or in combination with other treatments/medicaments for preventing or treating cancer selected from the group consisting of adrenal cancer, bone cancer and brain cancer that show therapeutic efficacy.

The term "physiologically acceptable carrier" refers to solvents, diluents, binders, adhesives, adjuvants, excipients, acceptors, stabilizer, analogues, flavoring agents, sweetening agents, emulsifying agents or preservative agents, which are well known to persons of ordinary skill in the art, for manufacturing pharmaceutical or dietary compositions.

The terms "administering" or "administration" as used herein refer to the methods that may be used to enable delivery of the composition or medicament of the present invention to the desired site of biological action. These methods include, but are not limited to, oral, intraduodenal, nasal, parenteral injection (including intravenous, subcutaneous, intramuscular, intravascular or intradermal), topical and rectal administration. In a preferred embodiment, the composition and medicament described herein are administered orally.

Unless otherwise required by context, singular terms shall include the plural and plural terms shall include the singular.

An objective of the present invention is to provide a medicament for preventing or treating cancer selected from the group consisting of adrenal cancer, bone cancer and brain cancer.

The aim of the present invention is to provide methods and/or medicaments for preventing or treating cancer selected from the group consisting of adrenal cancer, bone cancer and brain cancer.

One aspect of the invention is to provide a method for inhibiting tumor cell growth, comprising contacting an adrenocortical tumor cell with a composition comprising a therapeutically effective amount of at least one type of xanthophyll.

Another aspect of the invention is to provide a method for preventing or treating cancer selected from the group consisting of adrenal cancer, bone cancer and brain cancer, comprising administering to a subject in need thereof a composition comprising a therapeutically effective amount of at least one type of xanthophyll.

In the practice of the methods of the invention, a composition comprising a therapeutically effective amount of at least one type of xanthophyll is administered to a subject, e.g., a human subject, in need of the treatment and/or invention to inhibit the growth of tumor cells.

In the practice of the methods of the invention, xanthophylls from any sources can be used, whether natural or synthetic. According to a preferred embodiment of the invention, the xanthophyll is astaxanthin and/or an ester thereof. In a particularly preferred embodiment of the invention, the astaxanthin is derived from a natural source, such as a culture of the algae *Haematococcus* sp., e.g., *Haematococcus pluvialis*. *Haematococcus pluvialis* microalgae is a preferred natural, commercially available source of the astaxanthin used in the methods of this invention. In another preferred embodiment of the invention, the astaxanthin is chemically synthesized. Synthetic methods for preparing astaxanthin are known (R. D. G. Cooper et al., J. Chem Soc. Perkins Trans. I, (1975) p. 2195; F. Kienzle, H. Mayer, Helv. Chim. Acta., (1978) Vol. 61, p. 2609) as are methods of isolating astaxanthin from natural sources (Tischer, Z. Physiol. Chem., (1941) Vol. 267 p. 281; Seybold and Goodwin, Nature, (1959) Vol. 184, p. 1714). Thus, astaxanthin can be administered in a pure form as synthesized or isolated from natural sources.

Alternatively, and as a preferred embodiment of the methods of the invention, astaxanthin is administered as part of a composition comprising protein, carbohydrate, and fatty acids. When *Haemotococcus pluvialis* algae meal is used as the source of astaxanthin, the composition is preferably administered as derived from the microalgae, comprising the natural protein, carbohydrate, and fatty acid components of the microalgae. Such microalgae is commercially available (Cyanotech Corporation, Kailua-Kona, Hi.) and generally comprises as major components (by weight) from about 1.5 to 2% astaxanthin, about 15 to 30% protein, about 35 to 40% carbohydrates, about 10 to 25% ash, about 5 to 20% fat, and about 3 to 10% moisture. The composition further comprises minor components including iron, magnesium, calcium, biotin, L-carnitine, folic acid, niacin, pantothenic acid, and vitamins B1, B2, B6, B12, C, and E.

The present invention also provides a composition for preventing or treating cancer selected from the group consisting of adrenal cancer, bone cancer and brain cancer comprising a therapeutically effective amount of at least one type of xanthophyll and a physiologically acceptable carrier.

The present invention further provides a use of xanthophylls in the manufacture of a medicament for preventing or treating cancer selected from the group consisting of adrenal cancer, bone cancer and brain cancer.

The route of administration of the composition or medicament for preventing or treating cancer selected from the group consisting of adrenal cancer, bone cancer and brain cancer according to the present invention may be either oral or parenteral. The dosage form is selected appropriately according to the route of administration. Examples thereof include parenteral solutions, infusion solutions, powders, granules, tablets, capsules, pills, enteric-coated preparations, troches, liquids for internal use, suspensions, emulsions, syrups, liquids for external use, poultices, nose drops, ear drops, eye drops, inhalants, ointments, lotions, suppositories, and enteral nutrients. These can be used either alone or in combination depending on the condition of a disease. To prepare these dosage forms, auxiliary substances commonly used in the field of pharmaceutical manufacturing technology, such as excipients, binders, antiseptics, antioxidants, disintegrators, lubricants, and flavoring agents, can be used as necessary.

The dose of the xanthophylls for preventing or treating cancer selected from the group consisting of adrenal cancer, bone cancer and brain cancer according to the present invention varies depending on the purpose of administration or the individual to whom it is to be administered (gender, age, body weight, etc.). In a preferred embodiment of the invention, the therapeutically effective amount of xanthophylls is from about 0.1 mg to about 10 g, preferably about 1 mg to about 4 g, more preferably about 4 mg to about 500 mg, per day in case of oral administration; or about 0.01 mg to about 5 g, preferably about 0.1 mg to about 2 g, more preferably about 0.1 to about 500 mg, per day in case of parenteral administration.

The composition according to the present invention can be used not only as pharmaceuticals as described above, but also as the category of products regulated as "quasi-drugs," cosmetics, functional food products, nutritional supplements, foods and drinks, and other similar products. When used as quasi-drugs or cosmetics, the composition may be used in conjunction with various auxiliary substances commonly used in the field of quasi-drugs or cosmetics, or other technologies, if necessary. Alternatively, when used as functional food products, nutritional supplements, or foods and drinks, the agent may be used in conjunction with additives commonly used for food products, for example, sweeteners, spices, seasonings, antiseptics, preservatives, germicides, and antioxidants, if necessary. The agent may be used in a desired form such as solution, suspension, syrup, granule, cream, paste, or jelly, or may be shaped, if necessary. The ratio of the ingredients contained in these products is not particularly limited, and can be selected appropriately according to the intended purpose, the mode of usage, and the dosage.

The composition or medicament of the invention can be used alone or in combination with other treatments. In one preferred embodiment, the composition or medicament is for use in combination with radiation therapy and/or chemotherapy. In another preferred embodiment, the composition or medicament is administered simultaneously or separately with one or more therapeutic agents for preventing or treating adrenocortical cancer selected from the group consisting of adrenal cancer, bone cancer and brain cancer or managing the symptoms or complications of adrenal cancer, bone cancer and brain cancer.

Having now generally described the invention, the same may be more readily understood through reference to the following examples, which provide exemplary protocols for the production of the pharmaceutical composition of the invention and their use in the enhancement of the treatment of acute stroke. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1

Inhibition of Adrenal Tumor Cell Line

Cell Culture and Drug Treatment

Mouse adrenocortical Y1 cell line (ATCC, ATCC® CCL-79™) was grown in Dulbecco's modified Eagle medium (DMEM)-F12 supplemented with 10% fetal bovine serum at 37° C. in a humidified atmosphere at 5% $CO_2$.

Astaxanthin (Model NO: ATP-9601A; Yuan Yu Bio-Tech (Taiwan), Co., Ltd) was dissolved in dimethyl sulfoxide (DMSO) at concentration of 20 mM as stock solution.

The Y1 cells were incubated with DMSO or 40 μM of astaxanthin for 1, 2 or 3 days before analysis.

MTT Assay

Cells were washed with PBS after the treatment, followed by addition of 1 ml MTT (3-(4,5-cimethylthiazol-2-yl)-2,5-diphenyl tetrazolium bromide) solution (2 mg/ml in PBS) in each well. After incubation for 3 hours at 37° C., 2 ml of DMSO was added and cells were incubated in the dark for 30 minutes. Absorbance was measured at the wavelength of 570 nm (OD570).

Results

Figure 1B:
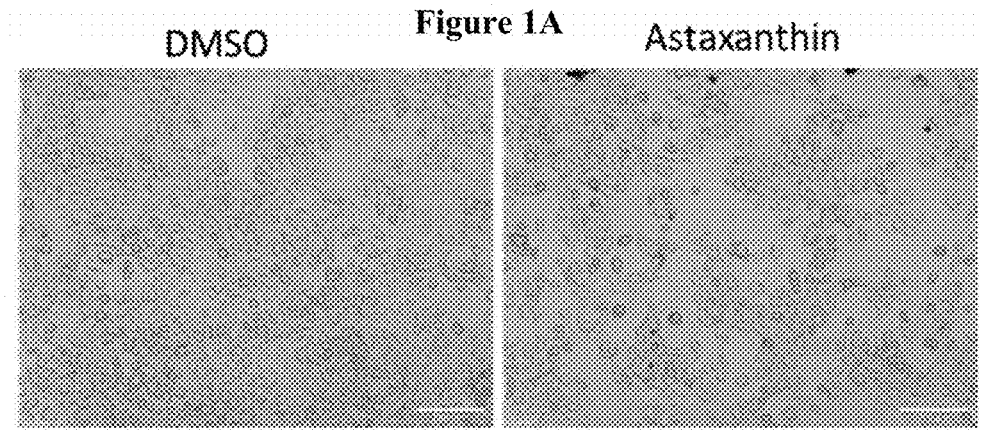
Figure 2:
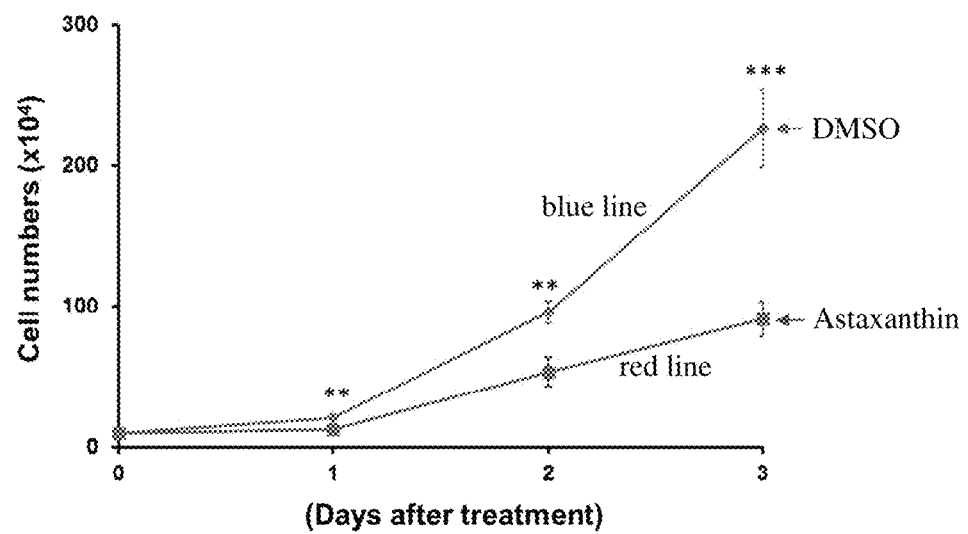
FIG. 2 shows the growth curve of Y1 cells after astaxanthin treatment (blue line) and DMSO treatment (red line). Cells were counted each time from four independent experiments and the mean±S.D. is shown.

After 1, 2 or 3 days of treatment, the number of Y1 cells in the astaxanthin treated group was reduced as compared with that in the control (DMSO treated) group (see FIGS. 1 and 2). This result was further confirmed by MTT assay, which measures the activity of mitochondrial succinate dehydrogenase and is indicative of cell viability.

Figure 3:
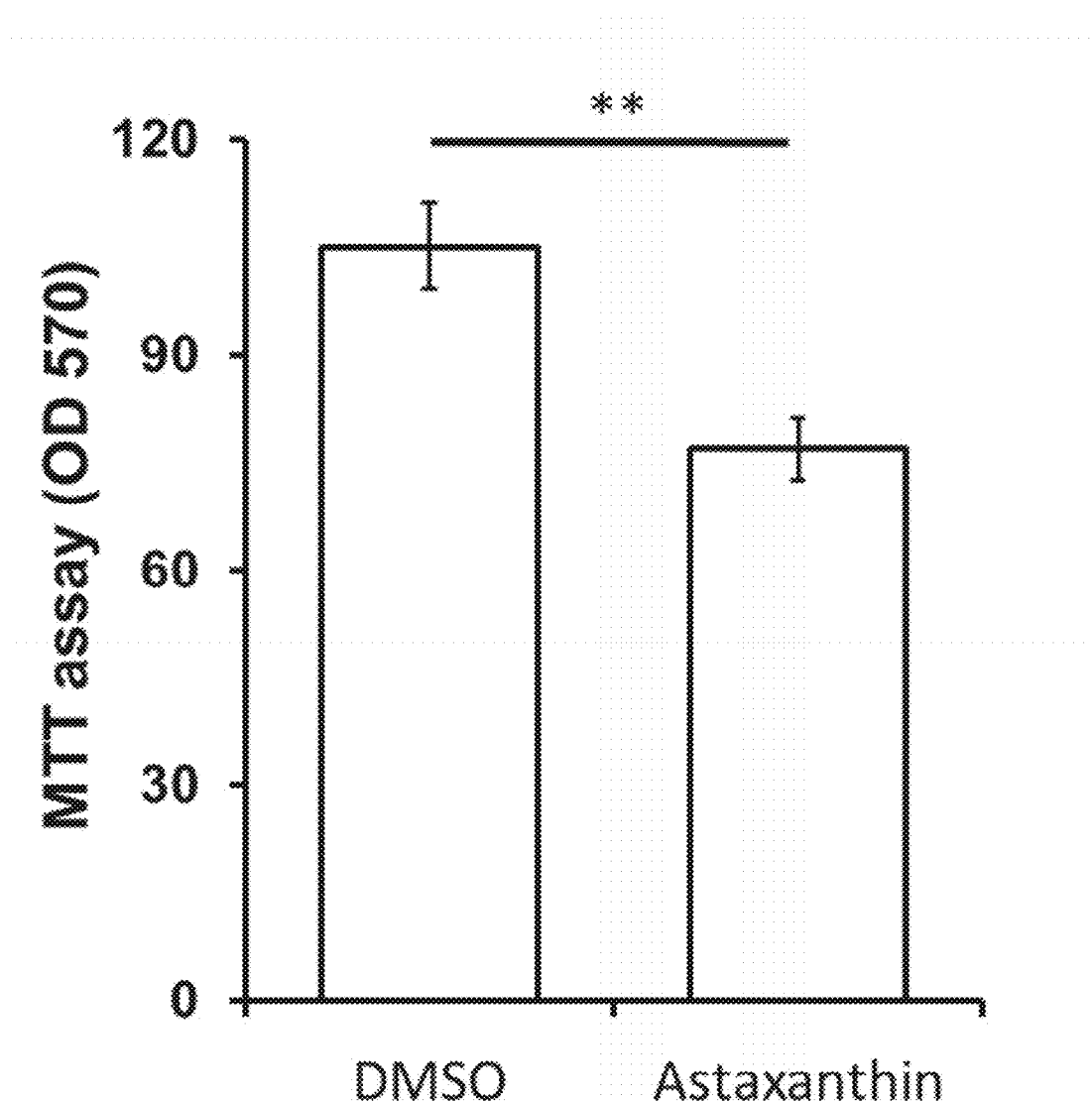
FIG. 3 shows the quantification of the population of viable Y1 cells in the presence of DMSO or astaxanthin. ** denotes P<0.01 as compared to control (DMSO treated) group.

As shown in FIG. 3, after astaxanthin treatment for 48 hours, the OD570 of the treatment group was reduced as compared with that of the DMSO treated group. The data can prove that astaxanthin efficiently inhibits adrenocortical tumor cell growth.

Example 2

Inhibition of Brain Tumor Cell Lines

Cell Culture and Drug Treatment

Human U87MG (ATCC, ATCC® HTB-14™) cell line was grown in DMEM medium supplemented with 10% fetal bovine serum at 37° C. in a humidified atmosphere at 5% $CO_2$. M059K (ATCC, ATCC® CRL-2365™) and M059J (ATCC, ATCC® CRL-2366™) cell lines were grown in Dulbecco's modified Eagle medium (DMEM)-F12 supplemented with 10% fetal bovine serum at 37° C. in a humidified atmosphere at 5% $CO_2$.

Astaxanthin was dissolved in dimethyl sulfoxide (DMSO) at concentration of 20 mM as stock solution.

The U87MG, M059K, and M059J cell lines were treated with DMSO or 100, 200 or 400 μM of astaxanthin for 24 hours or 48 hours and cell numbers were counted.

Results

Figure 4:
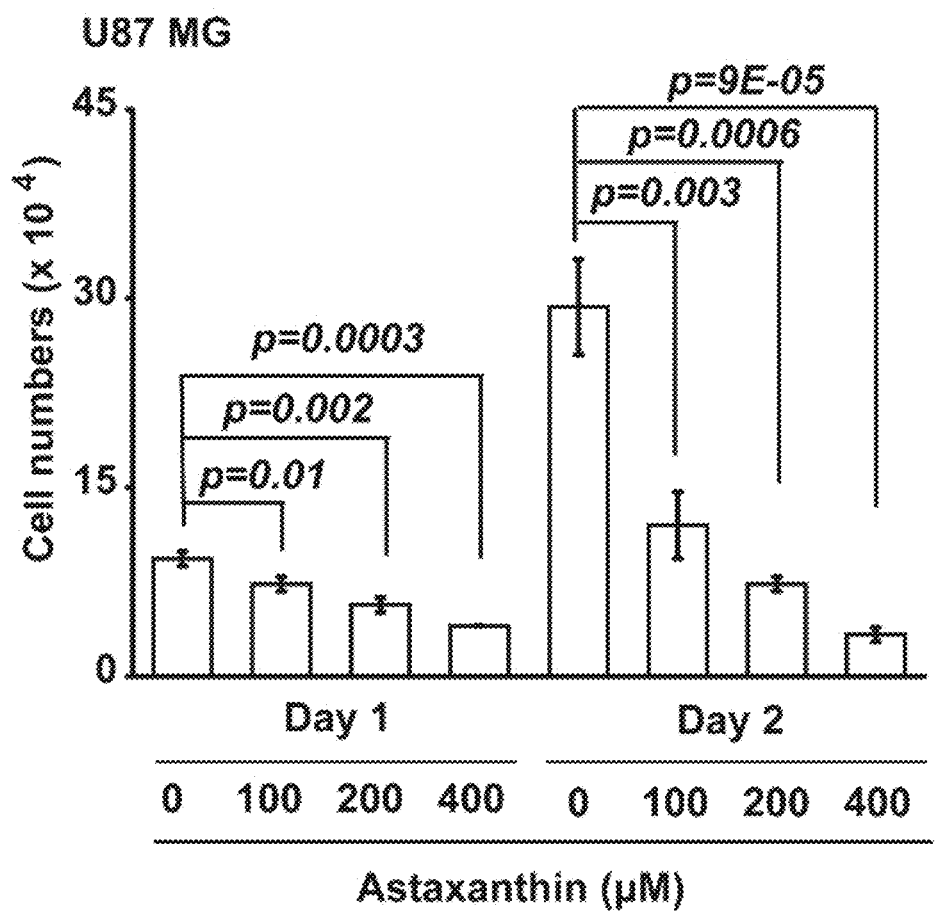
FIG. 4 shows reduced U87MG cell number after astaxanthin treatment. Cells were counted each time from four independent experiments and the mean±S.D. is shown.
Figure 5A:
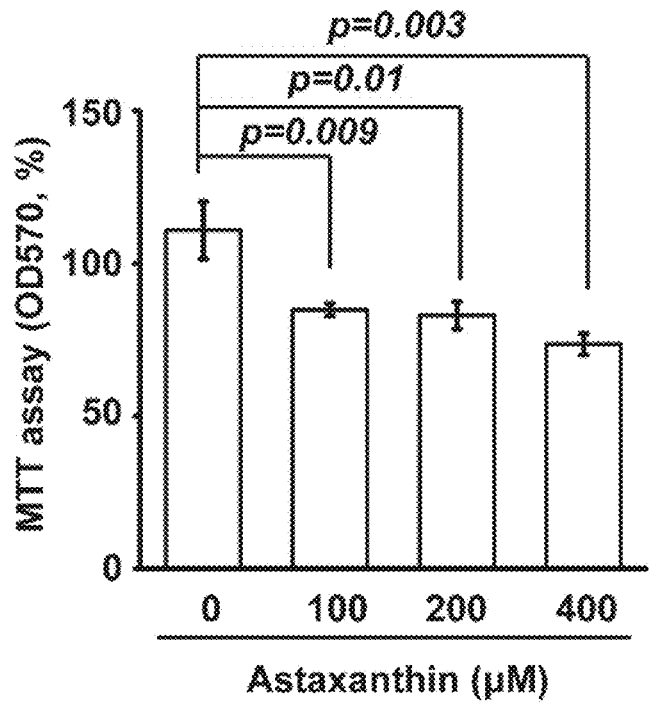
FIGS. 5A and 5B show that the viability of U87MG cells was reduced upon astaxanthin treatment. The population of viable U87MG cells was quantified in the presence of DMSO or different concentrations of astaxanthin.
Figure 5B:
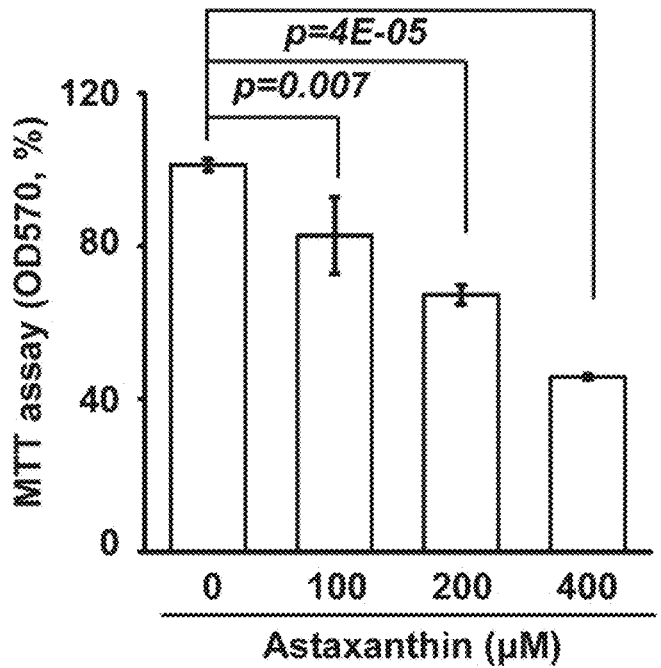
Figure 6:
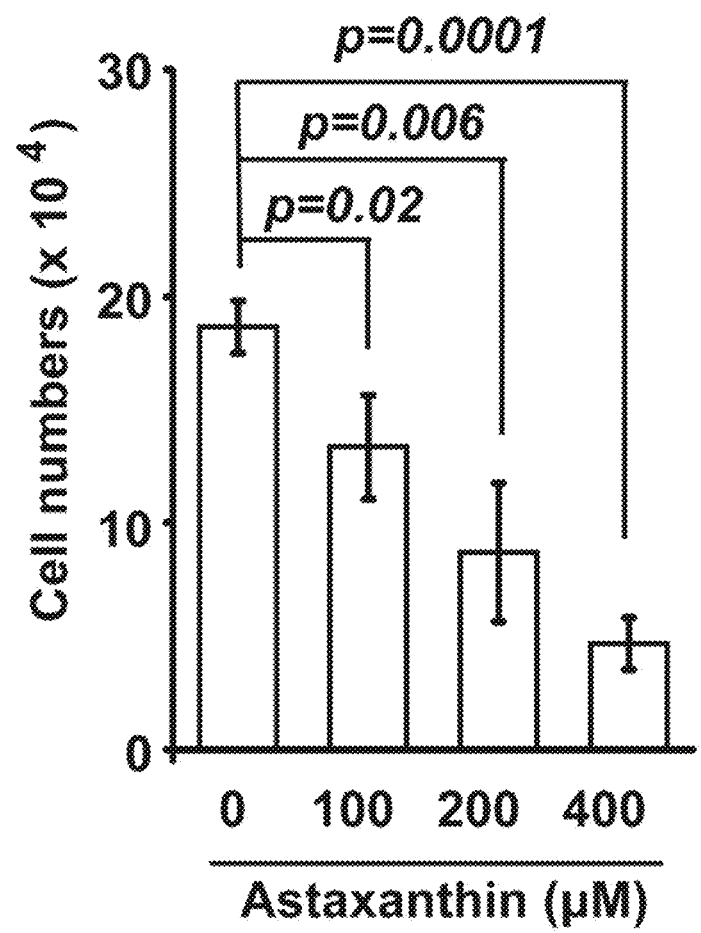
FIG. 6 shows reduced M059K cell number after astaxanthin treatment. Cells were counted each time from four independent experiments and the mean±S.D. is shown.
Figure 7:
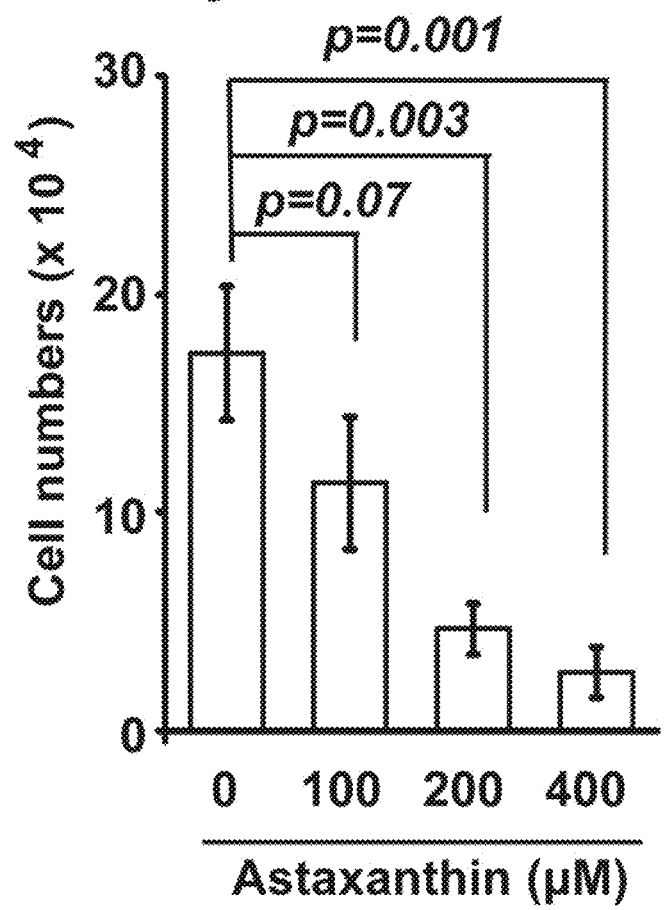
FIG. 7 shows reduced M059J cell number after astaxanthin treatment. Cells were counted each time from four independent experiments and the mean±S.D. is shown.

As shown in FIG. 4, astaxanthin inhibited U87MG cell growth in a dose-dependent and time-dependent manner. The data were also confirmed by MTT assay (see FIG. 5). As shown in FIGS. 6 and 7, astaxanthin also inhibited M059K (FIG. 6) and M059J (FIG. 7) cell growth. These data demonstrated that treatment with astaxanthin inhibited glioblastoma cell growth in a dose-dependent manner. Without being limited by theory, it is believed that astaxanthin can penetrate BBB (blood-brain barrier), indicating that astaxanthin might function as an anti-glioblastoma compound.

Example 3

Inhibition of Bone Tumor Cell Line

Cell Culture and Drug Treatment

Human U2OS (ATCC, ATCC® HTB-96™) cell line was grown in DMEM medium supplemented with 10% fetal bovine serum at 37° C. in a humidified atmosphere at 5% $CO_2$.

Astaxanthin was dissolved in dimethyl sulfoxide (DMSO) at concentration of 20 mM as stock solution.

The U2OS cell line was treated with DMSO or 100, 200 or 400 μM of astaxanthin for 72 hours and cell numbers were counted.

Results

Figure 8:
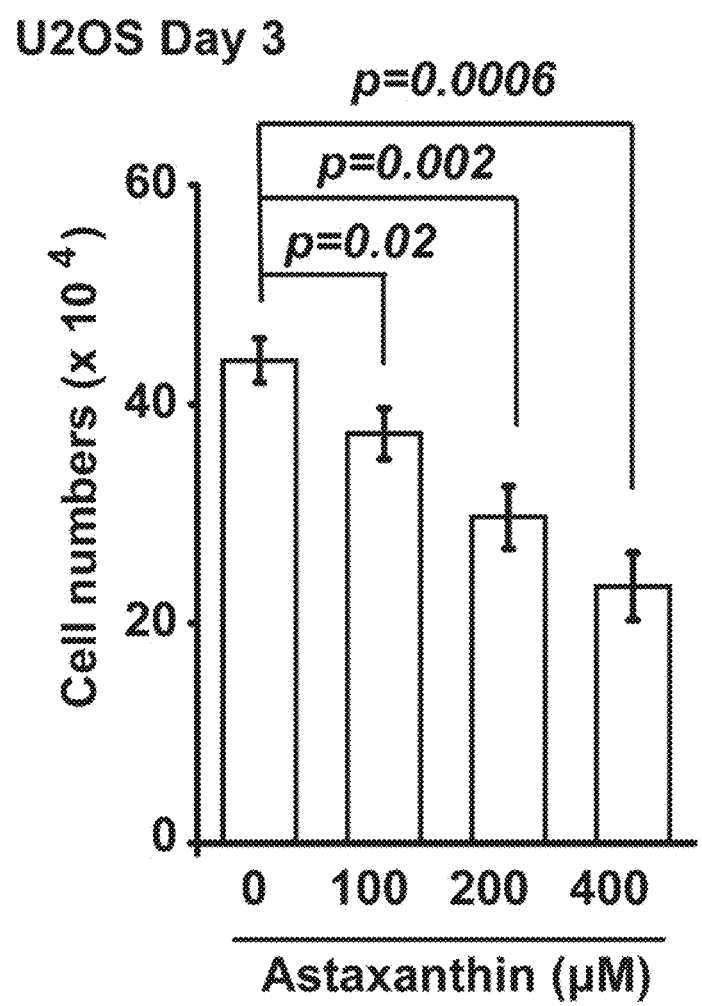
FIG. 8 shows reduced U2OS cell number after astaxanthin treatment. Cells were counted each time from four independent experiments and the mean±S.D. is shown.

As shown in FIG. 8, astaxanthin inhibited U2OS cell growth in a dose-dependent manner. These data demonstrate that treatment with astaxanthin inhibited osteosarcoma cell growth in a dose-dependent manner. The data can prove that astaxanthin efficiently inhibits osteosarcoma cell growth.

These data demonstrate that the xanthophylls (astaxanthin) can efficiently inhibit adrenocortical tumor, bone tumor and glioblastoma growth without any radiation therapy and/or chemotherapy.

Numerous modifications and variations of the invention as set forth in the above illustrative examples are expected to occur to those skilled in the art. Consequently, only such limitations as appear in the appended claims should be placed on the invention.

REFERENCES

Aldape, K., G. Zadeh, S. Mansouri, G. Reifenberger, and A. von Deimling. 2015. Glioblastoma: pathology, molecular mechanisms and markers. *Acta neuropathologica*.

Alifieris, C., and D. T. Trafalis. 2015. Glioblastoma multiforme: Pathogenesis and treatment. *Pharmacology & therapeutics*.

Else, T., A. C. Kim, A. Sabolch, V. M. Raymond, A. Kandathil, E. M. Caoili, S. Jolly, B. S. Miller, T. J. Giordano, and G. D. Hammer. 2014. Adrenocortical carcinoma. *Endocrine reviews*. 35:282-326.

Erickson, L. A., M. Rivera, and J. Zhang. 2014. Adrenocortical carcinoma: review and update. *Advances in anatomic pathology*. 21:151-159.

Higuera-Ciapara, I., L. Felix-Valenzuela, and F. M. Goycoolea. 2006. Astaxanthin: a review of its chemistry and applications. *Critical reviews in food science and nutrition*. 46:185-196.

Hussein, G., U. Sankawa, H. Goto, K. Matsumoto, and H. Watanabe. 2006. Astaxanthin, a carotenoid with potential in human health and nutrition. *Journal of natural products*. 69:443-449.

Kavitha, K., J. Kowshik, T. K. Kishore, A. B. Baba, and S. Nagini. 2013. Astaxanthin inhibits NF-kappaB and Wnt/beta-catenin signaling pathways via inactivation of Erk/MAPK and PI3K/Akt to induce intrinsic apoptosis in a hamster model of oral cancer. *Biochimica et biophysica acta*. 1830:4433-4444.

Khan, S. K., T. Malinski, R. P. Mason, R. Kubant, R. F. Jacob, K. Fujioka, S. J. Denstaedt, T. J. King, H. L. Jackson, A. D. Hieber, S. F. Lockwood, T. H. Goodin, F. J. Pashkow, and P. F. Bodary. 2010. Novel astaxanthin prodrug (CDX-085) attenuates thrombosis in a mouse model. *Thrombosis research*. 126:299-305.

Kim, Y. J., Y. A. Kim, and T. Yokozawa. 2009. Protection against oxidative stress, inflammation, and apoptosis of high-glucose-exposed proximal tubular epithelial cells by astaxanthin. *Journal of agricultural and food chemistry*. 57:8793-8797.

Kowshik, J., A. B. Baba, H. Giri, G. Deepak Reddy, M. Dixit, and S. Nagini. 2014. Astaxanthin inhibits JAK/STAT-3 signaling to abrogate cell proliferation, invasion and angiogenesis in a hamster model of oral cancer. *PloS one*. 9:e109114.

Park, J. S., J. H. Chyun, Y. K. Kim, L. L. Line, and B. P. Chew. 2010. Astaxanthin decreased oxidative stress and inflammation and enhanced immune response in humans. *Nutrition & metabolism*. 7:18.

Sasaki, Y., N. Kobara, S. Higashino, J. C. Giddings, and J. Yamamoto. 2011. Astaxanthin inhibits thrombosis in cerebral vessels of stroke-prone spontaneously hypertensive rats. *Nutrition research*. 31:784-789.

Song, X. D., J. J. Zhang, M. R. Wang, W. B. Liu, X. B. Gu, and C. J. Lv. 2011. Astaxanthin induces mitochondria-mediated apoptosis in rat hepatocellular carcinoma CBRH-7919 cells. *Biological & pharmaceutical bulletin*. 34:839-844.

Stupp, R., M. E. Hegi, W. P. Mason, M. J. van den Bent, M. J. Taphoorn, R. C. Janzer, S. K. Ludwin, A. Allgeier, B. Fisher, K. Belanger, P. Hau, A. A. Brandes, J. Gijtenbeek, C. Marosi, C. J. Vecht, K. Mokhtari, P. Wesseling, S. Villa, E. Eisenhauer, T. Gorlia, M. Weller, D. Lacombe, J. G. Cairncross, R. O. Mirimanoff, R. European Organisation for, T. Treatment of Cancer Brain, G. Radiation Oncology, and G. National Cancer Institute of Canada Clinical Trials. 2009. Effects of radiotherapy with concomitant and adjuvant temozolomide versus radiotherapy alone on survival in glioblastoma in a randomised phase III study: 5-year analysis of the EORTC-NCIC trial. *The Lancet. Oncology*. 10:459-466.

Wu, Q., X. S. Zhang, H. D. Wang, X. Zhang, Q. Yu, W. Li, M. L. Zhou, and X. L. Wang. 2014. Astaxanthin activates nuclear factor erythroid-related factor 2 and the antioxidant responsive element (Nrf2-ARE) pathway in the brain after subarachnoid hemorrhage in rats and attenuates early brain injury. *Marine drugs*. 12:6125-6141.

Zhang, X. S., X. Zhang, Q. Wu, W. Li, C. X. Wang, G. B. Xie, X. M. Zhou, J. X. Shi, and M. L. Zhou. 2014a. Astaxanthin offers neuroprotection and reduces neuroinflammation in experimental subarachnoid hemorrhage. *The Journal of surgical research*. 192:206-213.

Zhang, X. S., X. Zhang, M. L. Zhou, X. M. Zhou, N. Li, W. Li, Z. X. Cong, Q. Sun, Z. Zhuang, C. X. Wang, and J. X. Shi. 2014b. Amelioration of oxidative stress and protection against early brain injury by astaxanthin after experimental subarachnoid hemorrhage. *Journal of neurosurgery*. 121:42-54.

What is claimed is:

1. A method for inhibiting tumor cell growth, comprising contacting the tumor cell with a composition comprising a therapeutically effective amount of astaxanthin and/or an ester thereof, wherein the tumor cell is selected from the group consisting of an adrenal tumor cell, a bone tumor cell and a brain tumor cell.

2. A method for treating cancer selected from the group consisting of adrenal cancer, bone cancer and brain cancer, comprising administering to a subject in need thereof a composition comprising a therapeutically effective amount of astaxanthin and/or an ester thereof.

3. The method of claim 2, wherein the adrenal cancer is selected from the group consisting of adrenocortical adenoma, adrenocortical carcinoma, neuroblastoma and pheochromocytoma.

4. The method of claim 3, wherein the adrenal cancer is adrenocortical carcinoma.

5. The method of claim 2, wherein the bone cancer is selected from the group consisting of osteoma, osteoid osteoma, osteochondroma, osteoblastoma, enchondroma, giant cell tumor of bone, aneurysmal bone cyst, fibrous dysplasia of bone, osteosarcoma, chondrosarcoma, Ewing's sarcoma and fibrosarcoma.

6. The method of claim 5, wherein the bone cancer is osteosarcoma.

7. The method of claim 2, wherein the brain cancer is selected from the group consisting of gliomas, meningiomas, pituitary adenomas and nerve sheath tumors, preferably anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme (GBM), gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma and trilateral retinoblastoma.

8. The method of claim 7, wherein the brain cancer is glioblastoma multiforme.

9. The method of claim 2, wherein the astaxanthin and/or an ester thereof are derived from a natural source and/or are chemically synthesized.

10. The method of claim 9, wherein the astaxanthin and/or ester thereof are derived from a culture of the algae *Haematococcus* sp.

11. The method of claim 10, wherein the algae *Haematococcus* sp. is *Haemotococcus pluvialis*.

12. The method of claim 2, where the therapeutically effective amount of astaxanthin an/or an ester thereof is from about 0.01 mg to about 10 g per day.

13. The method of claim 2, wherein the composition is for use alone or in combination with radiation therapy and/or chemotherapy.

14. The method of claim 2, wherein the composition is administered simultaneously or separately with one or more therapeutic agents for treating cancer selected from the group consisting of adrenal cancer, bone cancer and brain cancer, or managing the symptoms or complications of adrenal cancer, bone cancer and brain cancer.

15. The method of claim 2, wherein the cancer has been surgically removed from the subject.

* * * * *